United States Patent [19]

Chion

[11] Patent Number: 5,074,850
[45] Date of Patent: Dec. 24, 1991

[54] EXTRACORPOREAL GASTROINTESTINAL DEVICE

[75] Inventor: Paulette Chion, Naugatuck, Conn.

[73] Assignees: Anthony Chion, Centerport; William B. Saltzman, East Northport, both of N.Y.

[21] Appl. No.: 520,722

[22] Filed: May 8, 1990

[51] Int. Cl.$^5$ .............................................. A61M 1/00
[52] U.S. Cl. .................................. 604/327; 604/320; 604/322; 604/323
[58] Field of Search ................. 251/86, 210, 212, 215, 251/227, 245; 128/748, 912; 604/327, 320, 322-332

[56] References Cited

U.S. PATENT DOCUMENTS

| | | | |
|---|---|---|---|
| 3,604,267 | 9/1971 | Johns | 604/221 |
| 3,699,964 | 10/1972 | Ericson | 604/323 |
| 4,417,892 | 11/1983 | Meisch | 604/323 |
| 4,631,051 | 12/1986 | Harris | 604/9 |
| 4,834,108 | 5/1989 | Vaillancourt | 128/748 |
| 4,842,590 | 6/1989 | Tanabe et al. | 604/282 |
| 4,863,426 | 9/1989 | Ferragamo et al. | 604/282 |

*Primary Examiner*—Randy C. Shaw
*Assistant Examiner*—G. Gualtieri
*Attorney, Agent, or Firm*—Bauer & Schaffer

[57] ABSTRACT

An extracorporeal auxilliary device attachable to a percutaneous tube formed of tubular member having a universal adaptor at one end for attaching to the tube and an adaptor at the opposite end for attachment to a drainage bag. A plurality of ports provided with closures are located in the tubular member along the length thereof, and a clamp downstream from the ports for opening and closing access to the drainage bag. Food and medication is inserted into the patient's stomach through two ports, and air escapes through a third port. The device includes an appropriate drainage bag and may be made of plastic or rubber.

2 Claims, 1 Drawing Sheet

1

EXTRACORPOREAL GASTROINTESTINAL DEVICE

This invention relates to an auxilliary device for use with a relatively permanantly attached percutaneous gastrointestinal device.

BACKGROUND OF THE INVENTION

After abdominal surgery it is necessary for the gastrointestinal tract to be evactuated in order to relieve the stress on the patient and permit the tract to heal. Consequently, a percutaneous tube is sutured in a gastrostomy leading from the stomach or intestine to a collecting bag adjacent the patient. In such procedures, the patient must also be fed or given medication directly through his gastrointestinal tract since normal feeding is not possible. In order to do this the bag is removed, and the food or medication is inserted directly into the proximal end of the percutaneous tube. However, such a system presents a number of apparent disadvantages.

As illustrated in U.S. Pat. No. 4,057,065, a gastrointestinal tube is known which is provided at its proximal end with one or two lumens through which liquids may be introduced to effect decompression of the stomach or intestine simultaneously with the introduction of the tube into the body. The function here is only to facilitate entry of the tube, and once the tube is sutured in place in the gastrostomy tube, the proximal opening is connected in the usual manner to the bag.

The tube has to be frequently opened to remove the bag, and thus, potentional infection is always present. In addition, there is no provision for the escape of air, and the build-up of pressure from gas in the system causes pain and vomiting in the patient as well as the inability of the patient to tolerate feeding through the tube. Still further, accumulated fluids and food which the patient cannot absorb into his system normally or which are unable to travel from the stomach into and through the small intestine must be removed through the tube. Since the same tube is used for all these functions, it is most difficult to switch from mode to mode, and time is lost between evacuation and medication for example.

There exists, therefore, a need for an extracorporeal auxilliary gastrointestinal device which does not have such disadvantages and which simplifies the treatment of postoperative patients of the described type. The present invention fulfills such a need.

BRIEF STATEMENT OF THE INVENTION

In accordance with the invention, there is provided an extracorporeal auxilliary device for use with gastrointestinal percutaneous tubes placed into a patient comprising an elongated tubular member having an adaptor at one end for attachment to the percutaneous tube and an adaptor at its other end for attachment to a drainage bag, a plurality of ports located in the tubular member along the length thereof and a valve located in the tubular member downstream from the ports for opening and closing access to the drainage bag of the tubular member. The ports are closed by valves or caps suitable to facilitate feeding, delivery of medication and evacuation of gas.

The use of the present invention allows the postoperative patient to automatically and without assistance evacuate and pass gas, while permitting the nursing staff to feed and deliver medicine in an efficient, simple manner in a minimum amount of time and with a minimum chance of infection.

At the same time the auxilliary device is easily removable for cleaning, sterilization, and/or replacement without inconveniencing the patient or disturbing the percutaneous tube.

Full details of the present invention are set forth in the following description.

THE DRAWINGS

In order to understand the present invention more fully, attention is directed to the accompanying drawings which are to be taken in conjunction with the following detailed description of the invention and in which drawings.

DESCRIPTION OF THE PREFERRED EMBODIMENTS

Figure 1:
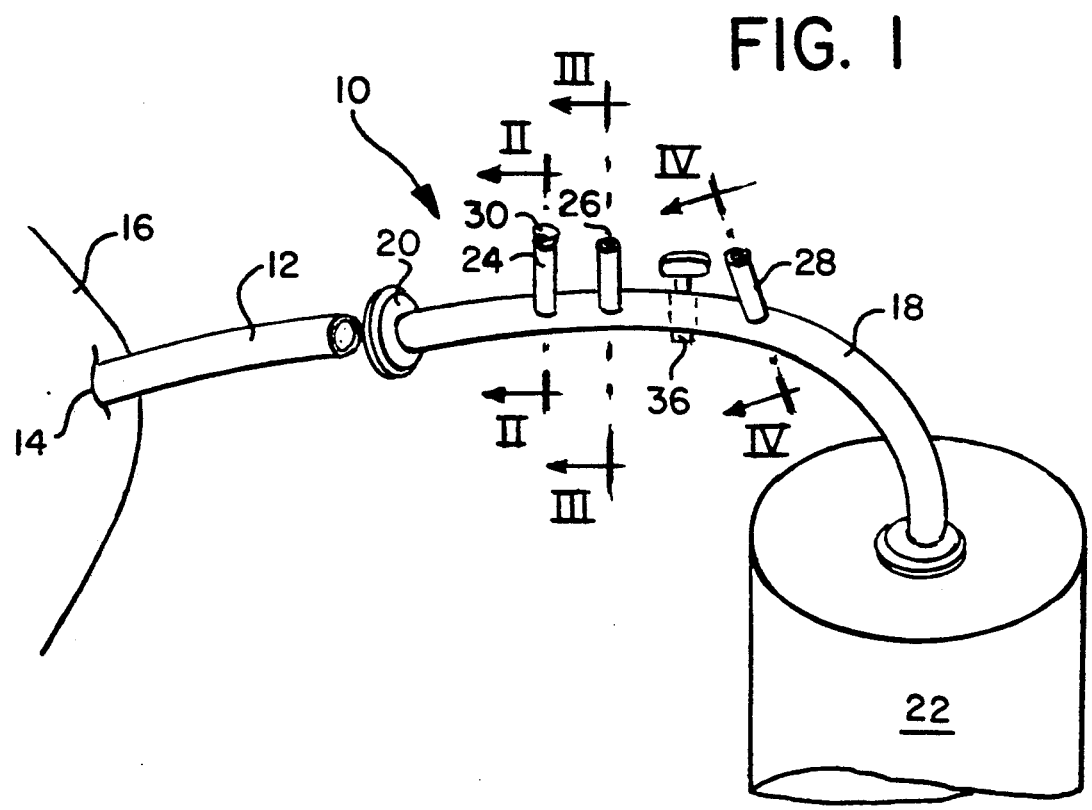
FIG. 1 is a diagrammatic lateral view in elevation of an extracorporeal gastrointestinal device according to the invention.
Figure 2:
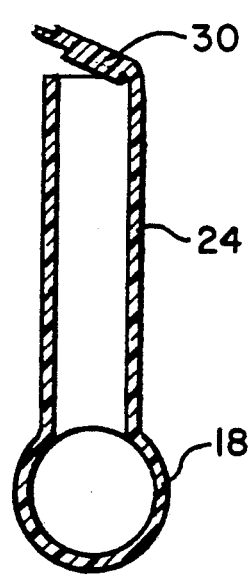
FIG. 2 is a sectional view along line II—II showing a port covered by a flap cap.
Figure 3:
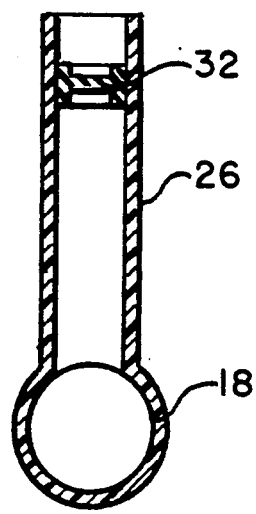
FIG. 3 is a sectional view along line III—III showing a self-sealing valve.
Figure 4:
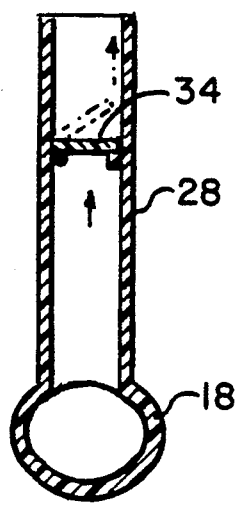
FIG. 4 shows an unidirectional valve.

The extracorporeal auxilliary device of the present invention generally depicted by the numeral 10 is shown in FIG. 1 as it would be applied to the proximal end of a conventional percutaneous tube 12, fixed in a gastrostomy 14 so that its distal end, not shown, is located in the stomach or the beginning of the small intestine of the patient 16. The auxilliary device 10 is a single, disposable unit comprising an elongated tube 18 made of flexible, conventional, and surgical plastic or rubber. The tube should be able to withstand thorough cleaning and sterilizational, and it is also beneficial that it be compatible with—that is, cause no significant irritation to, human body tissue, although this last attribute is not highly significant since the device is employed extracorporeally. Exemplative of useful rubber materials are vulcanized gum rubber, silicon rubber, butyl rubber, natural rubber, butadienestyrene rubber copolymers, and the like. Of these rubber materials silicon rubber is a preferred material. On the other hand, where a plastic material is employed to make the tubular member, it may be made from a polyamide such as nylon, a polyester such as polyhexamethylene tereplhthalate, a polyesteramide, a polyethylene, and the like. A preferred plastic material is polyethylene.

The elongated tube 18 is provided at its distal end with a universal adaptor 20 so that it may be removably connected to the proximal end of the percutaneous tube 12. Attached at the proximal end of the tube 18 is a similar adaptor to which is connected a drainage bag 22 of conventional design having a capacity of between 200 to 400 cc.

Located along the length of the tube 18 are a plurality of ports 24, 26, and 28. Port 24, which is closest to the patient 16, is adapted to introduce food and is provided with a spring-loaded flap type cap 30. The central port 26 is adapted so that medication or fluid may be inserted through it to the patient and may be provided with a self-sealing valve 32. The most proximal port 28 is for the elimination of air or gas and may be provided with a unidirectional outward valve 34. Port 28 is angled toward the patient so gas will not be expelled in the direction of the caregiver, and thus, fluid will not tend to escape at such an angle.

Located between ports 26 and 28 is a clamp 36 which is adapted to open and close passage through the tube 18 to the drainage bag 22 and prevents any return of the contents of the bag to the patient. It is also used to block access to the bag when the patient is being fed through port 24.

The overall length of the device is approximately 10 inches, although it may be longer if desired.

The auxilliary device of this invention provides many advantages. For example, it may be made from a wide variety of readily available, relatively inexpensive materials and can be fabricated by known plastics and rubber manufacturing methods for forming tubular structures.

The inventive device permits ready escape of accumulated gas from a patient, thus relieving pain and vomitting caused by the pressure of such gas if it cannot escape. The device also permits the ready disposal of accumulated fluids and foodstuffs which are unable to be absored into a patient's system or to travel from his stomach into and through his small intestine. Moreover, the device is readily attachable to or detachable from a feeding tube of different sizes already inserted into the patient as well as being readily attachable to and detachable from a drainage bag, thus making the collection and disposal of drainage a simple and quick operation. Still further, the pressure of the valve makes its possible to feed a patient with no escape of food or fluid into the drainage bag. Finally, since the device provides a closed system, there is less chance for infection. Numerous other advantages will be apparent to those skilled in the art.

While the auxilliary gastrointestinal device of this invention has been described in terms of certain specific embodiments, it is to be understood that numerous modification of the inventions may be made without departing from the spirit and scope of the invention. Therefore, it is to be understood that this invention is not to be limited to the specific embodiments described above, except as defined in the appended claims.

What is claimed is:

1. An extracorporeal auxiliary device for use with a percutaneous gastrointestinal tube comprising an elongated flexible tubular member having an adaptor at one end for extracorporeal attachment to said percutaneous tube, an adaptor at the opposite end for attachment to a drainage bag, a plurality of ports located in said tubular member along the length thereof, and clamp means located for allowing or preventing flow through said tubular member, first and second ports being located between said one end and said clamp means, one of said first and second ports being open for the introduction of food into said percutaneous tube and the other of said first and second ports having a self-sealing valve means for the syringe injection of medication into said percutaneous tube, and a third port located between said clamp and said other end having a unidirectional air valve for the expulsion of air from said drainage bag, said one of said first and second ports being provided with a hinged cap to normally maintain said ports closed.

2. The device according to claim 1, wherein said adaptors are elastic one being capable of resiliently connecting to said percutaneous tube and the other being capable of resiliently connecting to said drainage bag.

* * * * *